(12) United States Patent  (10) Patent No.: US 8,354,647 B2
Huebner et al.  (45) Date of Patent: Jan. 15, 2013

(54) PHOTOELECTRIC CHEMICAL SENSOR AND SENSING METHOD UTILIZING INTERFACIAL PHOTO-VOLTAGES

(75) Inventors: Jay S. Huebner, Jacksonville, FL (US); Rodolfo T. Arrieta, Panama City, FL (US)

(73) Assignee: University of North Florida, Jacksonville, FL (US)

( * ) Notice: Subject to any disclaimer, the term of this patent is extended or adjusted under 35 U.S.C. 154(b) by 1166 days.

(21) Appl. No.: 12/080,880

(22) Filed: Apr. 7, 2008

(65) Prior Publication Data

US 2008/0277590 A1    Nov. 13, 2008

Related U.S. Application Data

(60) Continuation-in-part of application No. 10/005,717, filed on Nov. 8, 2001, now Pat. No. 7,354,770, and a division of application No. 12/074,169, filed on Feb. 29, 2008.

(60) Provisional application No. 60/246,880, filed on Nov. 8, 2000.

(51) Int. Cl.
*G01J 1/42* (2006.01)
(52) U.S. Cl. .............. 250/393; 422/82.02; 422/82.09; 422/50; 422/500; 250/338.3; 436/147; 436/161
(58) Field of Classification Search ............ 422/50, 422/82.02, 82.09, 500; 250/393, 338.3; 436/147, 436/161
See application file for complete search history.

(56) References Cited

U.S. PATENT DOCUMENTS

| | | | |
|---|---|---|---|
| 4,806,490 A | 2/1989 | Bischoff et al. | |
| 4,883,579 A | 11/1989 | Humphries et al. | |
| 4,892,640 A | 1/1990 | Wolfbeis et al. | |
| 5,074,977 A | 12/1991 | Cheung et al. | |
| 5,125,737 A * | 6/1992 | Rodriguez et al. | 356/39 |
| 5,328,847 A | 7/1994 | Case et al. | |
| 5,413,915 A | 5/1995 | Case et al. | |
| 5,468,645 A | 11/1995 | Kirollos et al. | |
| 5,500,188 A | 3/1996 | Hafeman et al. | |
| 5,567,302 A | 10/1996 | Song et al. | |
| 5,599,717 A | 2/1997 | Vo-Dinh | |
| 5,622,868 A | 4/1997 | Clarke et al. | |
| 5,628,890 A | 5/1997 | Carter et al. | |
| 5,679,535 A | 10/1997 | Joyce et al. | |
| 5,936,730 A | 8/1999 | Foley et al. | |
| 5,938,617 A | 8/1999 | Vo-Dinh | |
| 5,981,287 A | 11/1999 | Sinclair et al. | |
| 6,130,097 A | 10/2000 | Polzius et al. | |

* cited by examiner

*Primary Examiner* — Jyoti Nagpaul
(74) *Attorney, Agent, or Firm* — Thomas C. Saitta (57) ABSTRACT

A device and method which comprises a sensing surface on a membrane, solid surface or electrode, where the sensing surface contains a photo-voltage active material chosen in relation to a particular target substance to be detected and quantified. The photo-voltage active material is of a type which produces an interfacial photo-voltage electrical signal upon illumination. The particular photo-voltage active material chosen for a particular target substance is one in which the presence of the target substance causes a change in the electrical signal produced. The presence of the target substance modifies the expected photo-voltage produced by the sensing surface upon illumination. The photo-voltage produces signals which are detected by electronic circuits, and the presence and concentration of the target substance is determined by analyzing the difference between the photo-voltage of the target sample versus the photo-voltage of a control sample lacking the target substance.

7 Claims, 9 Drawing Sheets

PHOTOELECTRIC CHEMICAL SENSOR AND SENSING METHOD UTILIZING INTERFACIAL PHOTO-VOLTAGES

This application is a continuation-in-part of U.S. patent application Ser. No. 10/005,717, filed Nov. 8, 2001, now U.S. Pat. No. 7,354,770 and U.S. Divisional patent application Ser. No. 12/074,169, filed Feb. 29, 2008, both claiming the benefit of U.S. Provisional Patent Application Ser. No. 60/246,880, filed Nov. 8, 2000. The disclosures of these two patent applications are incorporated by reference herein.

BACKGROUND OF THE INVENTION

This invention relates generally to the field of sensing devices and methods involving the detection of interfacial photo-voltages on an interfacial surface of a membrane or electrode to indicate the presence and amount of target chemical substances such as elements, compounds or molecules, both inorganic or organic within a solution, the photo-voltages being inter-atomic or inter-molecular. The devices and methods deal with interfacial charge transport where one medium making up the interface transmits electromagnetic radiation (IR through UV) and is simultaneously an electric conductor. More particularly, the invention relates to the field of devices and methods wherein particular photo-voltage active materials (PAMs) specific to the target chemical are deposited onto an electrode surface or a membrane and brought into contact with the target chemical analyte, wherein the PAMs generate interfacial photo-voltage electrical signals upon exposure to light, and wherein the difference in interfacial photo-voltages resulting from the presence of the target chemical relative to the expected photo-induced charge movements in the absence of the target chemical is analyzed to determine the presence of and the quantity of the target chemical present.

There are numerous instances where knowledge of the presence and quantity of a particular substance is required or desirable. Many qualitative and quantitative tests are known in the scientific arts. A number of these tests require either expensive equipment to analyze the test sample, analysis of the sample at a location remote from the sample collection location, or relatively long time periods to produce the result. It is an object of this invention to provide a device and a method which eliminates or reduces these drawbacks, where the detection and quantification of a target substance can be rapidly, accurately and relatively inexpensively achieved. As non-limiting examples, the invention may be used to detect and quantify metals including but not limited to Ac, Al, Ag, Am, Au, B, Ca, Cm, Co, Cr, Cu, Fe, Fl, Hf, I, In, K, Mg, Mn, Mo, Ni, Pa, Pb, Po, Pt, S, Th, Ti, U, Zn and Zr. Other target substances include but are not limited to dissolved gases, acid and alkaline phosphatases, dioxin, indole, nitrates, polysaccharides, sialomucins, skatole, sulfates, sulfomucins, trytophan, tyrosine, and uranic acid mucins. The invention can be used to detect the presence of and quantify particular strains of bacteria, viruses or other microorganisms, such as for example as a means to determine if water is sufficiently sanitized for drinking purposes. Bioreactors used to produce a wide range of products from brewers yeast to human insulin can be monitored. DNA, RNA, sugars and primary amines are other target substances which may be detected. Still other examples are illustrated in the disclosure to follow.

SUMMARY OF THE INVENTION

The invention comprises a device and method of using such device which comprises a sensing surface on a membrane, solid surface or electrode, where the sensing surface comprises a photo-voltage active material (PAM) chosen in relation to a particular target substance to be detected and quantified. The PAM is of a type which produces an interfacial photo-voltage electrical signal upon illumination by a light source. The interfacial photo-voltage is an inter-atomic or inter-molecular charge movement. The PAM chosen for a particular target substance is one in which the presence of the target substance causes a change in the interfacial photo-voltage electrical signal produced upon illumination. The target substance or analyte is added to a solution bathing the sensing surface to create a target sample, or a drop of solution may be placed onto the PAM. The presence of the target substance modifies the expected photo-voltage produced by the sensing surface upon illumination. The illumination is of short duration, and may be a single or multiple pulses of light within a chosen range of wavelengths. The interfacial photo-voltages produce electrical signals which are detected by electronic circuits, and the presence and concentration of the target substance is determined by analyzing the difference between the photo-voltage of the target sample versus the photo-voltage of a control sample lacking the target substance.

DETAILED DESCRIPTION OF THE INVENTION

Certain materials, referred to herein as photo-voltage active materials (PAMs) absorbed, adsorbed or otherwise deposited onto substrate surfaces such as membranes and electrodes generate transient electrical signals detectable on the surfaces of the membranes, electrodes or other substrates known as interfacial photo-voltages upon flash illumination. The photo-voltage signal generated over time may be monophasic, biphasic or triphasic.

Figure 1:
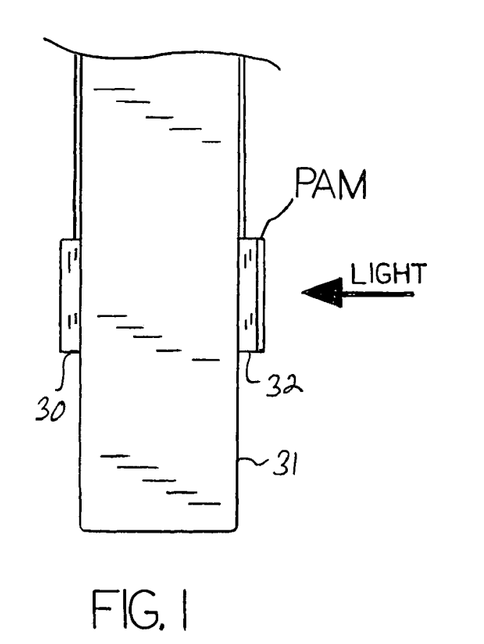
FIG. 1 shows a sensor embodiment having a single active electrode.
Figure 2:
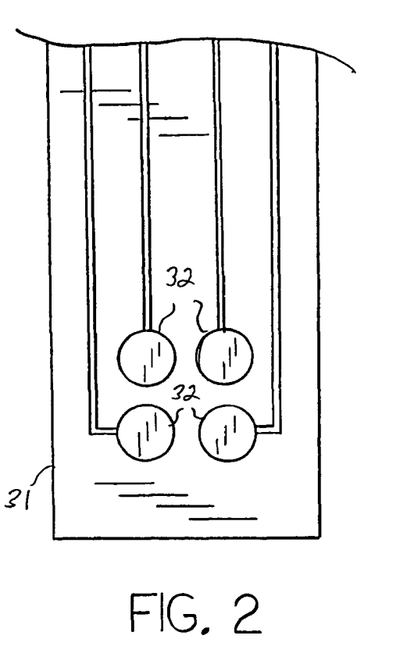
FIG. 2 shows a sensor embodiment having multiple active electrodes.

The substrate preferably comprises electrode structures, typically composed of noble metals, that can be immersed into a solution, such as a dual electrode having a first electrode 30 positioned on the back side of a circuit board or like material 31 which serves as a ground or reference, and a second or active electrode 32 positioned on the opposite side of the circuit board or like material 31 which is to be illuminated by a controlled light source (FIG. 1). Substrates 31 comprising multiple active electrodes 32, such as for example four active electrodes 32, may also be constructed and used in conjunction with multiple parallel channels to transmit data to multiple channel digital devices (an oscilloscope, an electrometer or a digital signal processor, for example) with multiple input channels (FIG. 2). In an alternative embodiment (FIG. 3), the electrodes 24 are mounted onto the side 21 of a container 13 and a ground electrode 23 is mounted onto another side, with signals being transmitted over channels 25. Each of the active electrodes is provided with a different PAM. Preferably, the multiple active electrodes are situated in close proximity such that a single illumination flash will initiate distinct interfacial photo-voltages at each electrode, the photo-voltages produced being of different amplitudes and time constants, and possibly even different polarities. The surfaces of the electrodes may be coated with parylene, self-assembled monolayers (SAMs), other coatings, or left bare. The SAMs themselves may be composed of PAMs, or may include PAMs during their formation, such as for example chlorophyll, or PAMs may be added onto the surface of the otherwise inert SAM.

The substrates or membranes may also comprise any thin dielectric film, such as for example Teflon, cellulose and polyvinylalcohol, preferably less than 5 microns in thickness and most preferably less than 1 micron, as well as self-assembled monolayers (SAMs), such as formed by adsorbing alkanethiols onto gold. Other plastics, polymers and proteins may be utilized, and different materials will offer advantages for different PAMs by allowing for different methods of bonding the PAM to the sensing surface.

In many circumstances the interfacial photo-voltage electrical signals generated by a particular PAM are modified by the presence of other chemical substances in such ways that the presence of these other substances can be detected and their amount determined by analyzing the difference in photo-voltages between a target solution containing the target chemical substance and a control solution which does not have the target chemical solution. Substances which may be detected include but are by no means limited to heavy metals, such as lead, mercury, cadmium and arsenic, some specific carbohydrates, sugars, dissolved oxygen, electrolytes, biochemicals, biomolecules, biological entities such as microorganisms, bacteria, and others. A solution's pH may also be determined. In some circumstances a dye or chromophore is a suitable PAM. Examples of some suitable PAMs or microbe receptors which result in differential photo-voltages in the presence of selected target substances are given in Table I. Some of these PAMs will also change color or produce heat, while others that produce suitable photo-voltages will not.

TABLE I

| Target Substance | Photo-voltage Active Material (PAM)/Microbe Receptor |
|---|---|
| ammonia | dye from Rose Art purple marker; and Tetrakis (pentafluorophenyl 21H,23H porphine). |
| aspirin | octaethyl porphine. |
| calcium | dis-R (8-(2-benzothiazolylamino)-6,7,7a,8a,9,10-hexahydrobis-(pyrido[2,1-b] benzothiazolo)[3,4-b:4',3'-e] pyridine-11-ium iodide), PAN (1-(2-pyridylazo)-2-napthol). |
| copper | bathocuproin; and dithizone. |
| dimethylmethyl phosphonate | meso-tetra phenyl phorphine (TTP); and phthalocyanine. |
| DNA, RNA | Stains-All (1-ethyl-2-{3-(1-ethylnaphtho[1,2-d] |

TABLE I-continued

| Target Substance | Photo-voltage Active Material (PAM)/Microbe Receptor |
|---|---|
| | thiazolin-2-ylidene)-2-methylpropenyl}naphtho[1,2-d]thiazolium bromide). |
| formaldehyde | 5,10,15,20-tetraphenyl 21H,23H porphine cobalt (II); and 5,10,15,20-tetraphenyl 21H,23H porphine iron (III) chloride. |
| glucose | rhodamine 3B (with boric acid). |
| iron | 4,7-diphenyl-1,10-phenanthroline; and benzo-{g,h,i}-perylenc-1,2-dicarboxylic acid hydrazide. |
| lead | 2,5-dimercapto-1,3,4-thiadiazole. |
| magnesium (II) | bathocuproin; and octaethyl porphine. |
| mercury | dibromofluroescein; dimethylaminobenzylidene rhodamine; rhodamine B; and Rutin. |
| methylphosphonic acid (MPA) | meso-tetra phenyl porphine (TTP). |
| model rocket propellant | octaethyl porphine. |
| nickel | dimethylglyoxime. |
| nitrate | protoporphyrin IX diethyl ester, 5,10,15,20-tetraphenyl 21H,23H porphine copper (II); and zinc 5,10,15,20 tetra(4 pyridyl) 21H,23H porphine. |
| oxygen | chlorophyll. |
| phosphate | magnesium phthalocyanine. |
| pyridine | octaethyl porphine; and meso-tetra(4-pyridyl) porphine. |
| solution pH value (2 PAMs needed) | Acridine and Napthol; and bromo-cresol purple and bromo-cresol green. |
| silver | 5-(4-dimethylaminobenzylidene)-rhodamine. |
| urea | magnesium phthalocyanine; and boron sub-2,3-naphthalocyanine. |
| zinc | PAN (1-(2-pyridylazo)-2-napthol); and 5,10,15,20-tetra(4 pyridy)-21H,23H porphine. |
| E. Coli | 5,10,15,20-tetra-phenyl 21H,23H porphine iron (III) chloride |
| Sindbis virus | Heparin Sulfate |
| Porcine parvovirus | 5,10,15,20-tetra-phenyl-(4 pyridyl)-21H,23H porphine |

A basic embodiment of the apparatus for the invention may include a digital oscilloscope and a flash light source such as a ns pulsed tunable laser, a xenon stroboscope or high intensity LEDs. The apparatus may be constructed using Burr-Brown OPA655 operational amplifiers with gain bandwidth product of 400 MHZ. The apparatus may use RG-62/U output coaxial cables which enables the amplifier's output to settle reasonably fast. Three different oscilloscopes have been used experimentally (Tektronics, Inc., Beaverton, OR and Hewlett-Packard, Colorado Springs, Colo.), with the Tektronics model 468 and the HP model 54522A being able to accomplish signal averaging. Both can be operated so that a set number of noise traces can be subtracted from the same number of signal plus noise traces (obtained by blocking the light impinging on the film), thus providing significant noise reduction beyond that available from the dual electrometer. Traces used for some of the experimental work were taken from the faster HP oscilloscope and digitally filtered. Preferably a digital signal processor is utilized in the system. The light source is controlled by a light trigger operated by a control panel, and the light is directed through appropriate filters and a beam splitter onto the membrane and a photocell. Dependent on the particular PAMs chosen, a full white spectrum or partial spectrums limited for example to UV or IR may be utilized.

Self-assembled monolayers (SAMs) incorporating PAMs on solid gold or other metal electrodes 22 must be illuminated from the monolayer side and cannot normally be illuminated through the metal, though transparent and electrically conducting electrodes 22, such as tin oxide, can be used with thinly sputtered gold to hold SAMs and so could be illuminated through the electrode 22. In different arrangements, the sensing surfaces on membranes 21 can be illuminated from either side, the side with the sensing PAM or the other side, with light passing through transparent membranes 21. The advantage of a transparent structure is that it would not require light to come through the test solution, which may contain materials what would reduce the light reaching the sensing surface. The PAMs may be bonded to the substrates using known mechanisms such as through hydrophobic bonds, electrostatic bonds, covalent bonds, etc.

A sample to be analyzed is suspended in an aqueous solution designed to dissolve the target chemical or substance, or alternatively a drop or small amount of the solution may be placed directly onto the PAM. A precise aliquot of the solution is placed in a measurement container or cuvette containing a measurement solution. The solution in the cuvette contacts a specially prepared surface, typically an electrode or polymer film membrane, having an adsorbed PAM on its surface that is sensitive to the presence of the target substance. Another similarly prepared surface is used as a blank and is not exposed to the solution containing the target substance. This control solution is used to establish a reference baseline. The target solution in the cuvette is thoroughly mixed and the cuvette is inserted into the charge displacement measurement apparatus. The cuvette contains an internal electrode, which is in electrical contact with the digital signal processing circuitry. The sensing surfaces of the membrane are exposed to light with a particular spectral content for a particular duration dependent on the chosen PAM, and the PAM produces an interfacial photo-voltage signal that is picked up by the internal electrode and an external electrode, which is also connected to the digital signal processor. The electrodes are preferably Ag/AgCl electrodes or the like provided with light shields. The interfacial photo-voltage signal induced by the illumination of the PAM is transmitted from the digital signal processor to the oscilloscope for analysis. The strength of the signal is proportional to the concentration of the target substance over the concentration range of interest when the proper PAM/analyte combination is utilized.

Samples to be analyzed may include stored products, air and other gases, liquids, solids, particulates gathered on filter media or adhesive or adsorbent members, or the like. The gathering media may be worn as badges on the body or clothing, or more direct gathering by direct contact with substrates containing or retaining the target substances, such as by using a vacuum to gather particulates onto a filter, may be utilized.

Some nitrogen-containing PAMS, such as aniline, carbazole, diphenylamine, guanine, 2-nitrotoluene and nitrobenzene for example, may be self-detecting, in that the presence of the substance alone in the target solution will yield a change in photo-voltage.

Figure 3:
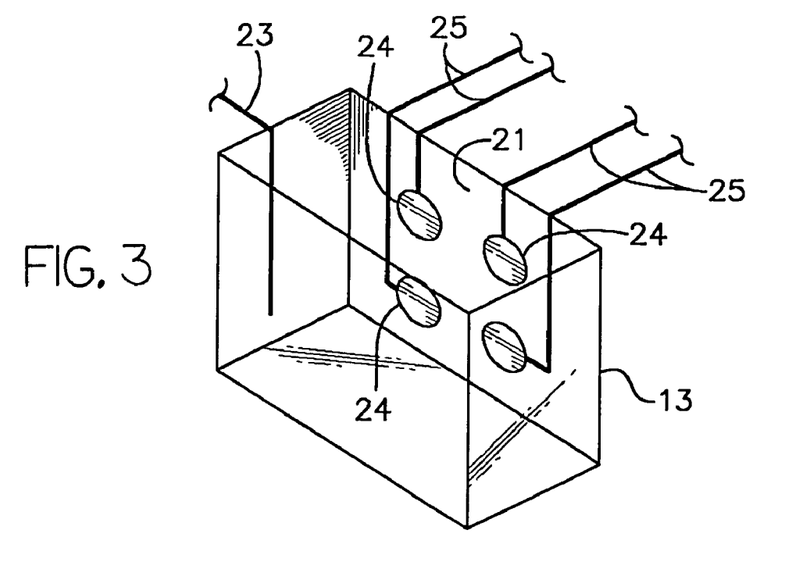
FIG. 3 shows an alternative sensor embodiment having multiple active electrodes.

A patterned array of different PAMs on a single polymer film membrane 21 or a substrate 31 (such as a circuit board) with multiple electrodes can be formed to produce a matrix of sensor patches 24/32, such as illustrated in FIGS. 2 and 3. The matrix allows a single membrane 21 or substrate 31 to be used to detect and quantify a plural number of target substances. The photo-voltage waveforms would be detected by individual electrode-electrometer channels 25, the outputs of which are digitized and interpreted. The results can be read out on a digital panel in near-real time and/or downloaded to other devices.

Figure 4:
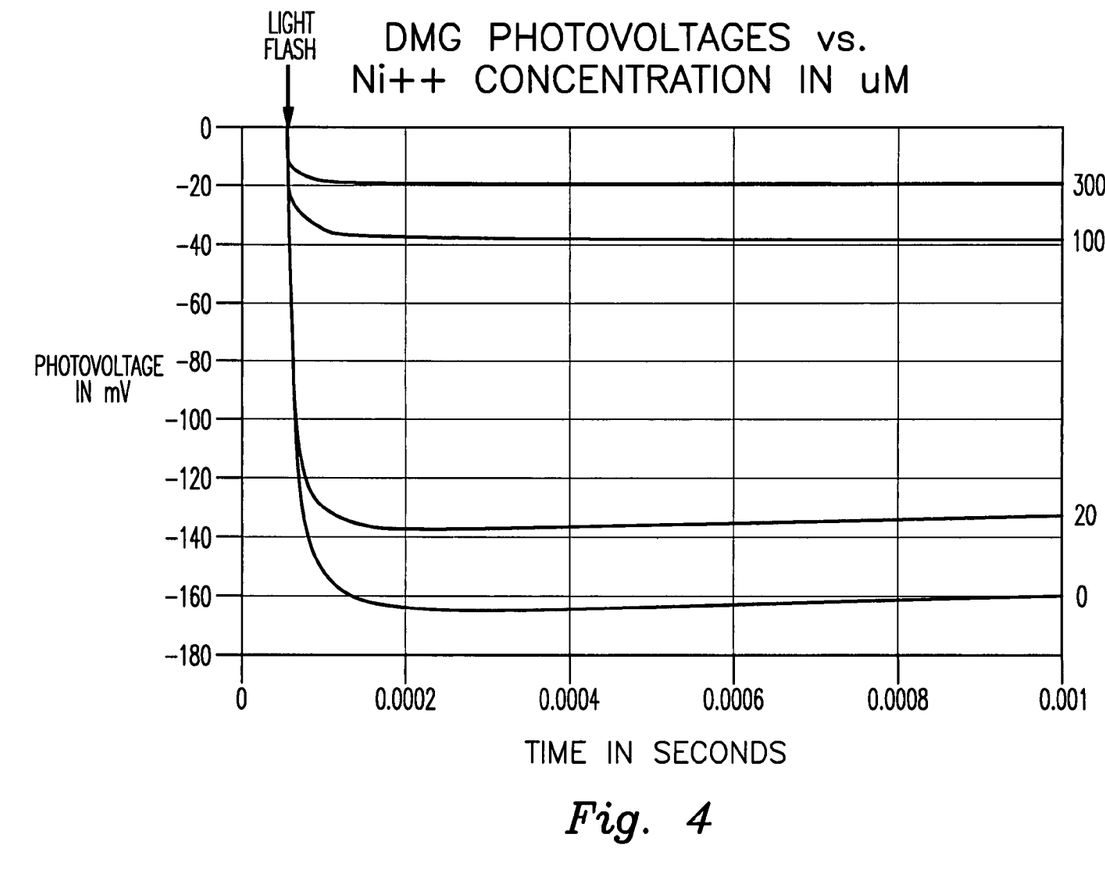
FIG. 4 is a plot of the PAM DMG photo-voltages resulting from differing $Ni^{++}$ concentrations.
Figure 5:
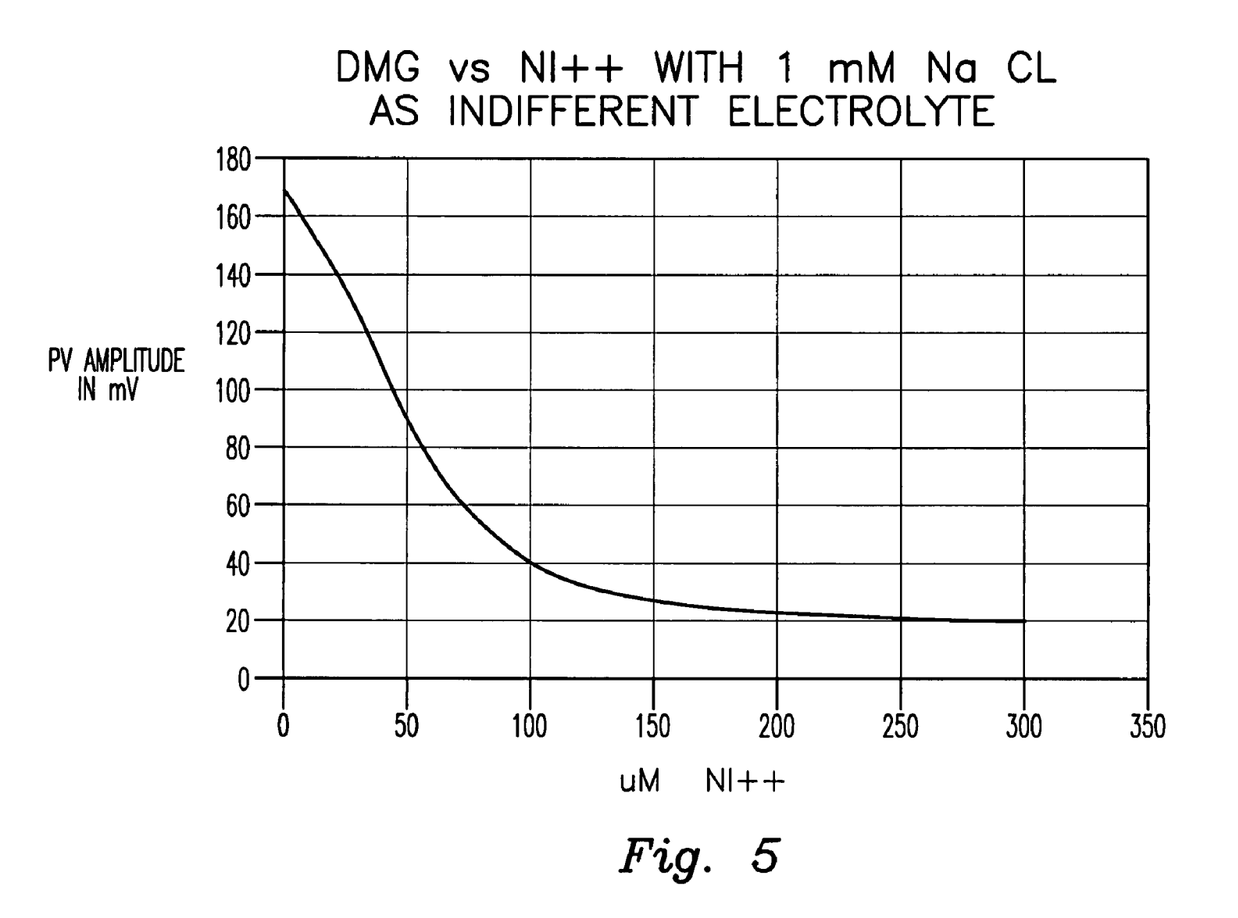
FIG. 5 is a plot of the amplitude data from FIG. 4, showing that the system and method is suitable for detecting the presence of and the amount of $Ni^{++}$ in the solution.

Films or electrodes coated with a variety of PAMs show sensitivity to the presence of various analytes. The most common mechanism is direct detection through complexation and either an increase or decrease of the photovoltage amplitude. FIGS. 4 and 5 show responsive photo-voltages for DMG in the presence of $Ni^{++}$ solutions of various concentrations, illustrating the device and method not only detect the prexence of target substances, but can be used to determine the concentration of the target substance in the solution.

Figure 6:
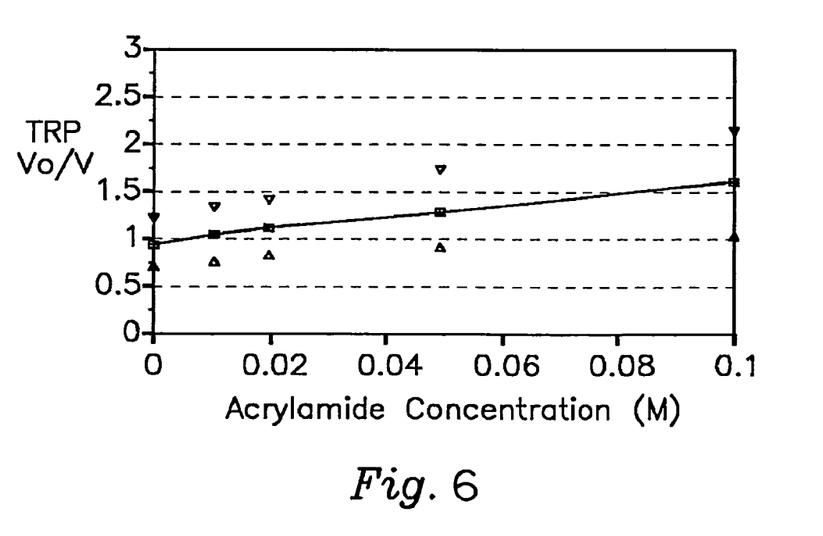
FIG. 6 is a corrected Stern-Volmer plot of acrylamide quenching of photo-voltages associated with excited state tryptophan.

Quenching of the electronic transitions that lead to photo-voltages also provides a result for an effective sensor design. FIG. 6 illustrates the quenching of tryptophan photo-voltages by acrylamide. Here linearization is achieved by assuming Stem-Volmer kinetics with a correction to remove the effects of static quenching. A variety of photo-voltage quenchers will be assayable using this approach. For example, oxygen is known to quench the excited singlet state of many molecules.

Figure 7:
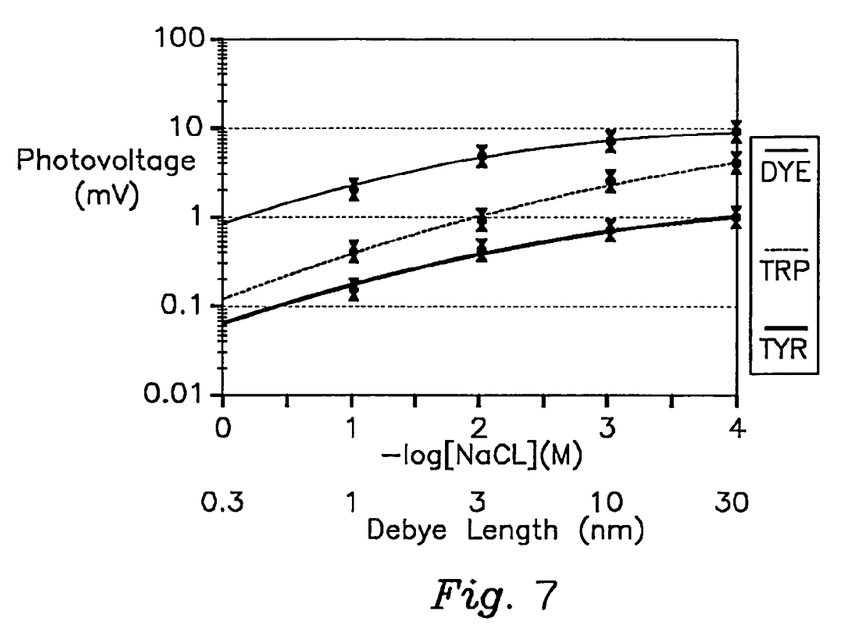
FIG. 7 is a plot of the electrolyte dependence of photo-voltages of several PAMs.
Figure 8:
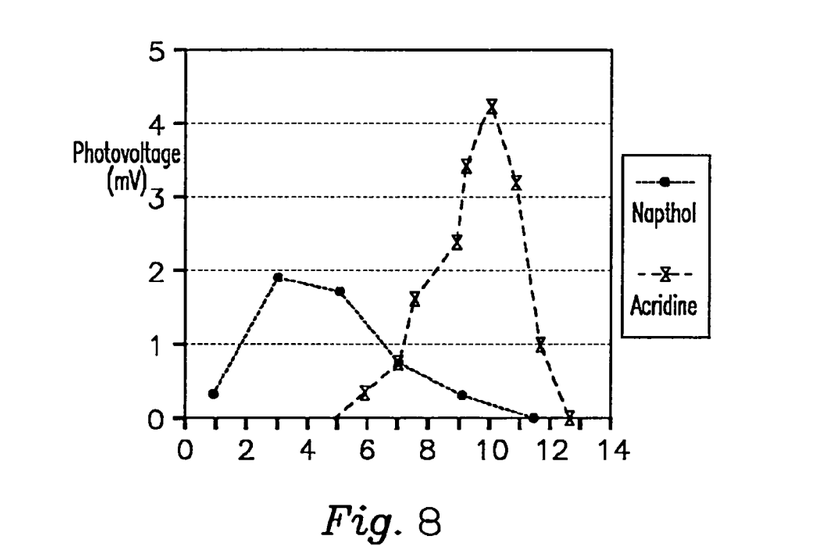
FIG. 8 is a plot of the dependence of photo-voltages on pH for two types of PAMs.

For a given sensor system, parameters such as electrolytic concentration must be determined, as this can have a profound effect on the signal amplitude. The electrolytic dependence of the PAMs Tryptophan (Trp) and Tyrosine (Tyr), both aromatic amino acids, and the carbocyanine PAM dye diO—$C_1$-3-Cl as taken on lipid-based films are illustrated in FIG. 7. Another environmental variable that can confound a given sensor system is pH. Several PAM families produce pH sensitive photo-voltages, with the examples naphthol and acridine being shown in FIG. 8 and representing opposite ends of the pH scale. The lowest excited singlet state of naphthols is more acidic than the ground state, owing to electron shifts which cause aromatic alcohol deprotonation under some conditions following light absorption. At high pH this photo-voltage is no longer possible because all the PAMs are deprotonated. On the other hand, acridine-type PAMs become a stronger base upon excitation, thus producing photo-voltages at higher pHs. Correspondingly, the use of two such families in a sensor array allows the sensor to measure pH and apply a pH correction to any other pH sensitive PAMs in the array.

Sensor self-calibration is important in continuous sensing applications. A ratiometric procedure based on a sequence of flashes can be used to determine the parameters to be used in the electrolytic self-calibration procedure. Further, many film-PAM combinations have been shown to have well-behaved isosbestic points which may be used to adjust for loss of active PAM due to a variety of degradation reactions. Another approach for recalibration involves PAMs that produce two distinct photo-voltage mechanisms. When the signals generated by these mechanisms have distinct rise and fall times, they can be separated using numerical techniques such as exponential peeling. If one mechanism is sensitive to an analyte and the other is not, the signal generated by the latter can be used to calibrate the former.

Transference of the signal filtering, film condition and pH correction algorithms into a Digital Signal Processor will allow for the creation of a physical sensor device based on a miniature flash lamp, analog-to-digital converter, DSP engine and sensor array, similar in size and ease of use to a disposable film camera.

Examples of successful PAM/target substance combinations which produce photo-voltages which can be sufficiently analyzed to produce evidence as to the presence of the target substance and typically its concentration follow.

EXAMPLE 1

The PAM 4,7-diphenyl-1,10-phenanthroline was adsorbed on a membrane. A strobe flash produced a positive signal of 2.6 mV at 20 microseconds after the strobe flash. This produced the control baseline. In the presence of 2.5 mM ferric (iron III) ions, the signal at 20 microseconds was 5.0 mV negative, showing that the presence of iron ions can be detected through the change in photo-voltage. Subsequent experimentation at lower iron concentrations indicate that 5 nanomolar changes in concentration are distinguishable.

EXAMPLE 2

The PAM, dimethyl glyoxime, was absorbed on parylene coated platinum electrode, and immersed in water containing 1 mM NaCl. A strobe flashes produced negative photo-voltage signals with −167 mV being recorded at 200 microseconds after the strobe flash, with 10× electrometer gain. $NiCl_2$ was added to give 20 micromolar $Ni^{++}$ concentration, which reduced the photovoltage amplitude to −140 mV. Additional $NiCl_2$ solution was added to raise the $Ni^{++}$ concentration to 100 micromolar, which reduced the photo-voltage amplitude to −39 mV. Additional $NiCl_2$ solution was added to raise the Ni++ concentration to 300 micromolar which reduced the photovoltage to −20 mV. These experiments demonstrate PV amplitude changes that are monotonically decreased with increased Ni++ concentrations. Data from this example is shown in FIGS. 4 and 5.

EXAMPLE 3

A membrane was prepared with the PAM dye Stains-All, a cationic carbocyanine dye, and a baseline from a control target sample was obtained. DNA was provided at a concentration of 0.1 microgram per ml in a target sample, and the photo-voltage signal was reduced at 0.5 milliseconds from positive 48 mV to less than positive 0.1 mV. Further experimentation showed that incremental additions of DNA in the target solution resulted in corresponding incremental reductions in the photo-voltage results.

EXAMPLE 4

A membrane was prepared with the PAM dye Stains-All, a cationic carbocyanine dye, and a baseline from a control target sample was obtained. RNA was provided at a concentration of 0.1 microgram per ml in a target sample, and the photo-voltage signal was reduced at 50 microseconds from positive 10 mV to negative 10 mV.

EXAMPLE 5

The detection of microorganisms such as bacteria is based on the polysaccharide fraction of bacterial lipopolysaccharides (LPS). This fraction is easily cleaved from the surface of bacterial cells through a variety of treatments, and comprises an O-antigen fraction which serologically defines a particular strain of bacteria and a core polysaccharide fraction which varies little among strains of a particular bacteria species. The core polysaccharides of the vast majority of Gram-negative bacteria start with a disaccharide of 3-deoxy-D-manno-octulosonic acid. This sugar (known as KDO) is almost exclusively found as part of LPS. The invention uses a sensitive polysaccharide sensor using KDO and its oligosaccharides. Crosslinked lipid monolayers supported on either side of an ultrathin plastic membrane are used as the substrate for signal transduction. The membrane's surfaces are covered with chemically selective sites and chromophoric centers that are sensitive to the occupation of the selective sites. The geometry allows nearly equivalent light energy to interact with both sides of the membrane, thus canceling out all variations except those caused by changes in the analyte concentration on the outside solution. The membrane is a differential sensor with the chemically unexposed side serving as the blank or control.

The sensing surface consists of a layered membrane structure that has been modified with two types of custom-designed molecules in special arrangements. One molecule is a monomer containing a reversible hydroxyl binding group, and the other is a reporting PAM. Both of these molecules are anchored to the membrane. Selective sites on the membrane are created with the reporter PAMs embedded therein. The assemblages are stabilized by chemical, electrochemical and/or photochemical crosslinking to fix the geometry of the selective sites, a process known as imprinting. The imprinting fixes the reactive groups in the right configuration to specifically recognize the analyte. Both the binding group molecules and chromophoric molecules also possess functional groups that allow them to bind to each other and to the membrane's lipid layers. To make the sensor selective to an analyte the sensor is exposed to the analyte and the membrane is crosslinked, which fixes the reactive groups in the right configuration to recognize the analyte. The sensor is then washed to remove the template.

The electrometer uses three mini-DIP OPA655 operational amplifiers in a design which cancels most of the radio frequency noise induced in proximate pulsed light sources by using a pair of electrodes, one sensing the photo-voltage induced signals and the other monitoring a cell of comparable geometry but with no PAMs. The design is implemented in surface mount technology to achieve multiple channels of the required density to implement the membrane sensor matrix. Stroboscopes may be utilized to produce the light flash illuminations. Filters may be utilized to modify the composition of illuminating spectra incident on individual membrane sections.

EXAMPLE 6

Another mechanism for inducing photo-voltages is photo-induced redox reactions. For example, experiments have been carried out using chlorophyll and NaI as a sensitive indicator of dissolved oxygen. In these experiments the photo-voltage decreases to 10% of its amplitude in air when the solution contacting the sensing surface is purged with nitrogen. The mechanism involves oxidation of the iodide anion by photo-excited chlorophyll and oxidation of the reduced ground state chlorophyll by oxygen. The net effect of these reactions is the production of large, lipophilic polyiodide anions that can permeate many types of non-polar films. The signal is quite large if the film is highly permeable to the polyiodide ions that are formed. An imposed transfilm voltage leads to observable photoinduced transfilm conductance changes which are proportional to the number of polyiodide ions permeating the film.

Photoinduced redox reactions that do not lead to transfilm conductance changes can also be detected through PAMs, provided that charged species are produced which undergo a net charge displacement transverse to the film-solution interface. Examples include amino acids, porphyrins, synthetic dyes, fullerenes and transition metal complexes such as bipyridine ruthenium II and ferricyanide.

EXAMPLE 7

The PAM, 2,2'-Biquinoline, was absorbed on a parylene coated platinum electrode and immersed in water containing 1 mM NaCl. A strobe flashes produced negative photo-voltage signals with −100 mV being recorded at 200 microseconds after the strobe flash, with 10× electrometer gain. $ZnCl_2$ was added to give 100 micromolar Zn++ concentration, which increased the photo-voltage amplitude to −139 mV.

Figure 9:
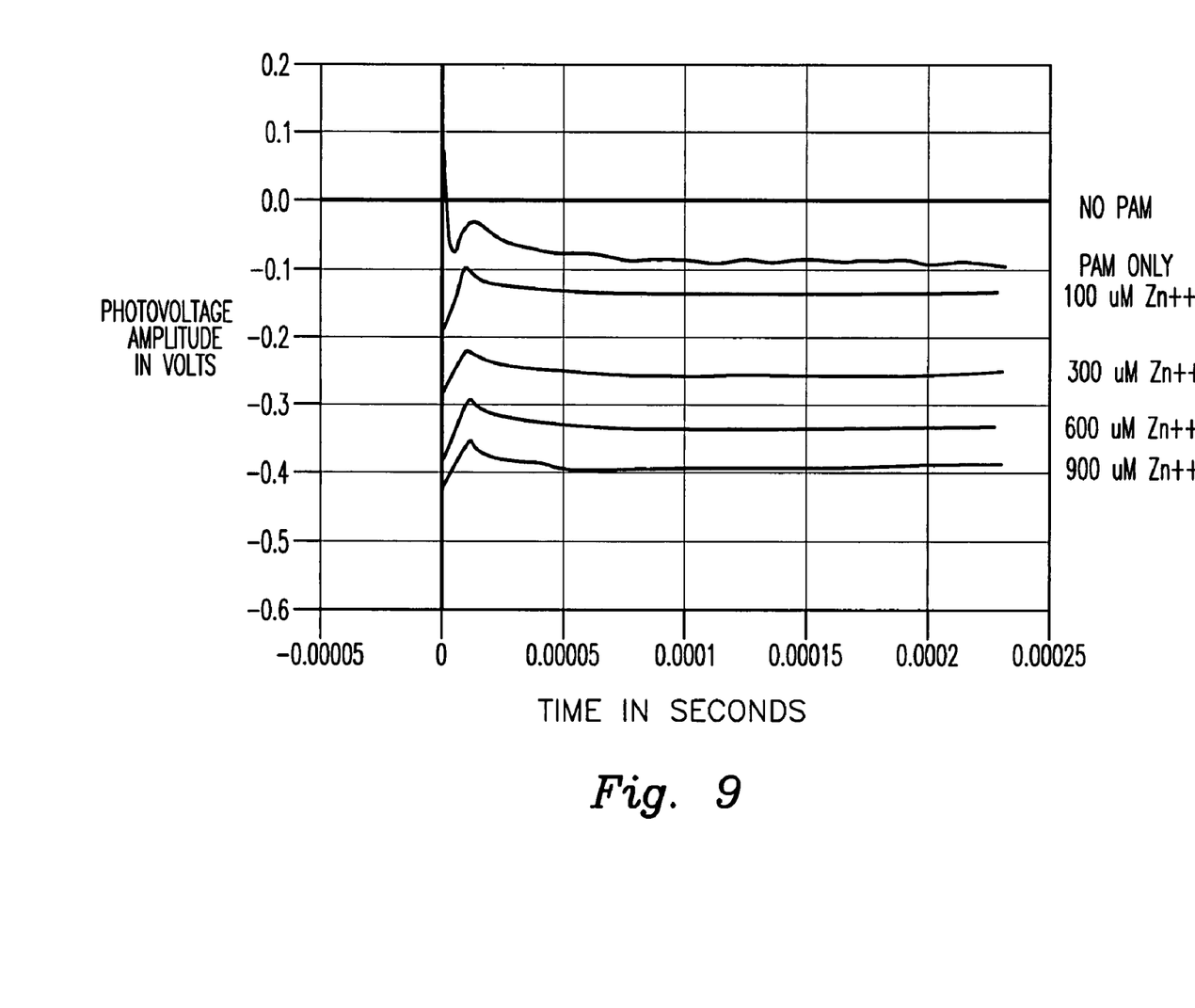
FIGS. 9 and 10 are plots similar to FIGS. 4 and 5, herein showing the PAM 2,2'-Biquinoline and detection of $Zn^{++}$.
Figure 10:
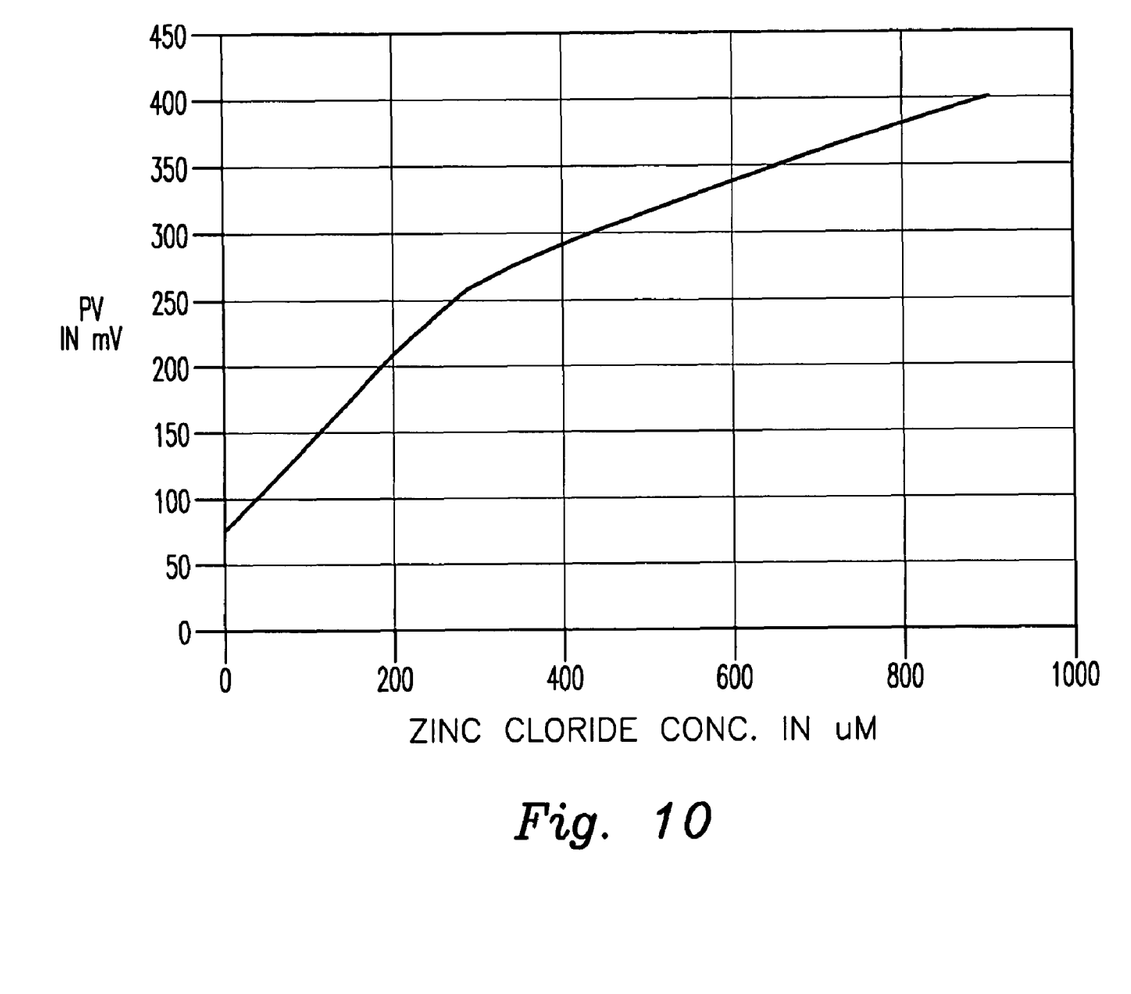

Additional ZnCl$_2$ solution was added, raising the Zn++ concentration to 300 micromolar, which increased the photo-voltage amplitude to 255 mV. Still more ZnCl$_2$ was added to raise the Zn++ concentration to 600 micromolar, which increased the photo-voltage amplitude further to −333 mV. Additional ZnCl$_2$ solution was added to raise the Zn++ concentration to 900 micromolar which increased the photo-voltage amplitude to −394 mV. This and other comparable experiments demonstrate PV amplitude changes that are monotonically increased with increased Zn++ concentrations. Results are shown in FIGS. 9 and 10.

EXAMPLE 8

Figure 11:
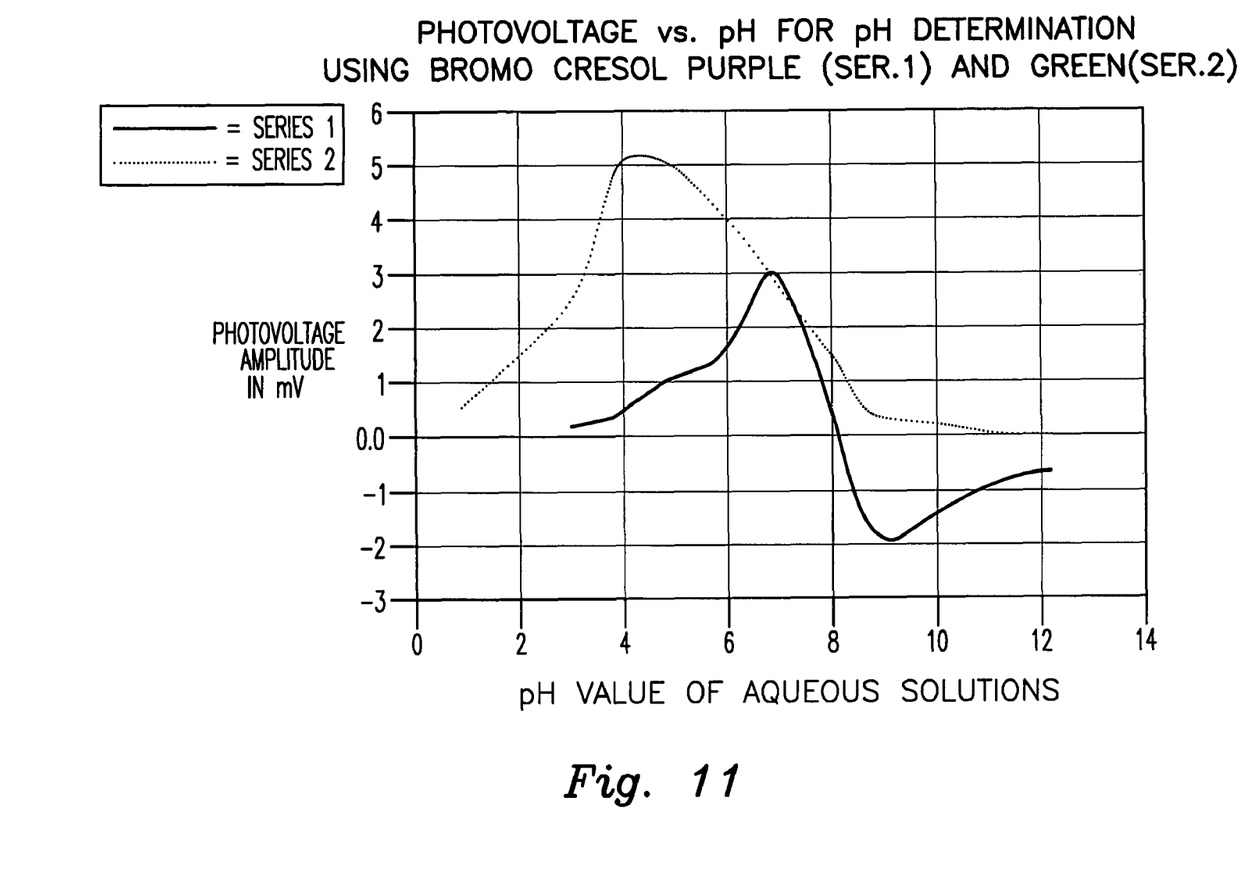
FIG. 11 is a graph of photo-voltage vs. pH for the PAM Bromo-cresol purple and green.

Bromo-cresol purple, also known as 5',5"-dibromo-o-cresolsulfophthalein (the PAM) was added to one side of a lipid bilayer membrane, and the membrane illuminated from the opposite side. The pH value of the membrane bathing solution was measured with a laboratory pH meter after subsequent procedures. The photo-voltage amplitude was measured (using an electrometer with 1×gain), . . . vs. pH values: 0.2 mV@ pH 3.09, 0.3 mV @ pH 3.9, 1.0 mV@ pH 4.9, 1.5 mV@ pH 5.9, 3.0 mV@ pH 6.8, 1.5 mV@ pH 7.7, −1.8 mV@ pH 8.8, −1.6 mV@ pH 9.89, −1.0 mV@ pH 11 and −0.7 mV@ pH 12.2. Bromo-cresol green was also tested. These experiments demonstrate the PVs of the bromo-cresol purple are positive with acidic pH values (3 to 8) but negative above 8. Results are shown in FIG. 11.

EXAMPLE 9

Figure 12:
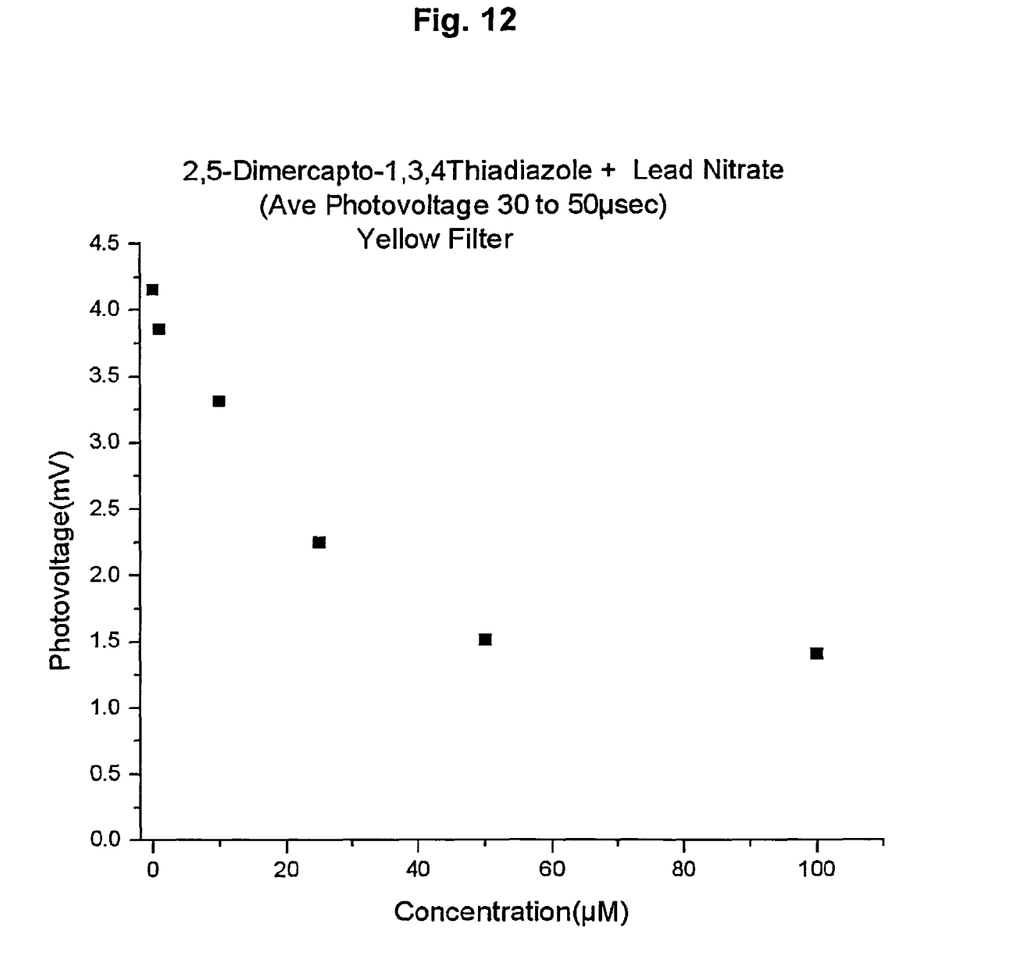
FIG. 12 is a plot similar to FIGS. 9 and 10, herein showing the PAM 2,5-dimercapto-1,3,4-thiadiazole and detection of lead nitrate.

Detecting lead in solution with the PAM 2,5-dimercapto-1,3,4-thiadiazole, using yellow light on a dual electrode produces the results shown in FIG. 12.

The methodology of the invention set forth above in fragmented form can be summarized as follows:

A method for detecting the presence of a target substance in a solution comprising the steps of:

providing a sensing device to sense the interfacial photo-voltage resulting from illumination of a PAM which is in contact with said target substance;

choosing a PAM which produces interfacial photo-voltage upon illumination and which produces a different amount of photo-voltage upon illumination when in contact with said target substance;

adsorbing said PAM onto a substrate;

illuminating said PAM;

detecting and analyzing the photo-voltage resulting from illumination of said PAM when not in contact with said target substance to provide a baseline value;

placing said target substance in solution in contact with said PAM;

illuminating said PAM;

detecting and analyzing the photo-voltage resulting from illumination of said PAM when in contact with said target substance;

comparing the baseline value results from illumination of said PAM when not in contact with said target substance to the results obtained from illumination of said PAM when in contact with said target substance to determine if said target substance is present;

successively detecting and analyzing the photo-induced charge movements resulting from illumination of said dye when in contact with different concentrations of said target substance to produce comparative concentration values;

comparing the results from illumination of said PAM when in contact with said target substance to the comparative concentration value results obtained from illumination of said PAM when in contact with different concentrations of said target substance to determine the concentration of said target substance;

wherein said illumination step is performed with a duration of milliseconds or less;

wherein said illumination step is performed over a chosen wavelength range.

The methodology set forth above may further comprise the steps of:

wherein said PAM is a first PAM and said target substance is a first target substance, further comprising the steps of:

successively detecting and analyzing the photo-voltage resulting from illumination of said first PAM when in contact with different concentrations of said first target substance to produce comparative concentration values;

comparing the results from illumination of said first PAM when in contact with said first target substance to the comparative concentration value results obtained from illumination of said first PAM when in contact with different concentrations of said first target substance to determine the concentration of said first target substance providing at least one PAM different from said first PAM and adsorbing said at least one different PAM onto said substrate, wherein said at least one different PAM produces photo-voltage upon illumination and which produces a different amount of photo-voltage upon illumination when in contact with a different target substance;

placing said different target substance in contact with said at least one different PAM simultaneously with placing said first target substance in contact with said first PAM;

illuminating said at least one different PAM simultaneously with illuminating said first PAM;

detecting and analyzing said photo-voltage from said at least one different PAM;

successively detecting and analyzing the photo-voltage resulting from illumination of said at least one different PAM when in contact with different concentrations of said different target substance to produce comparative concentration values;

comparing the results from illumination of said at least one different PAM when in contact with said different target substance to the comparative concentration value results obtained from illumination of said at lest one different PAM when in contact with different concentrations of said different target substance to determine the concentration of said different target substance.

It is understood that equivalents and substitutions for certain components and steps set forth above may be obvious to those skilled in the art, and therefore the true scope and definition of the invention is to be as set forth in the following claims.

We claim:

1. An apparatus for detecting the presence and concentration of a target substance in a solution through comparison of the differences in interfacial photo-voltages between a control solution and a target solution containing the target substance, wherein a photo-voltage active material is utilized which produces interfacial photo-voltage upon illumination and which produces a different amount of interracial photo-voltage upon illumination when in contact with said target substance, the apparatus comprising:

a light source for illumination;

a photo-voltage active material which produces interfacial photo-voltage upon illumination and which produces a different amount of interfacial photo-voltage upon illumination when in contact with said target substance, said photo-voltage active material being adsorbed onto the surface of an electrode positioned such that said photo-voltage active material is in contact with said target solution and such that said interfacial photo-voltage produced by said photo-active material upon illumination is transferred to said electrode;

a digital signal processor in electrical communication with said electrode to detect said photo-voltages and to generate a signal for analysis;

means to analyze said signal to determine the presence and concentration of said target substance.

2. The apparatus of claim 1, further comprising a container to receive a target solution containing a target substance, and wherein said electrode is disposed within said container.

3. The apparatus of claim 2, further comprising additional electrodes disposed within said container, each said electrode having a photo-voltage active material adsorbed thereon which produces interfacial photo-voltage upon illumination and which produces a different amount of interfacial photo-voltage upon illumination when in contact with said target substance, said photo-voltage active material being in contact with said target solution.

4. The apparatus of claim 3, wherein each of said adsorbed photo-voltage active materials on said electrode and said additional electrodes is a different photo-voltage active material.

5. The apparatus of claim 1, wherein said light source is chosen from the group of light sources consisting of lasers, stroboscopes and LEDs.

6. The apparatus of claim 1, wherein said electrode comprises a self-assembled monolayer.

7. The apparatus of claim 1, where said analyzer means is an oscilloscope.

* * * * *